United States Patent [19]

Puram et al.

[11] Patent Number: 5,347,128
[45] Date of Patent: Sep. 13, 1994

[54] DIRECTIONAL EMITTANCE SURFACE MEASUREMENT SYSTEM AND PROCESS

[75] Inventors: Chith K. Puram, Yorktown; Kamran Daryabeigi, Virginia Beach; Robert Wright; David W. Alderfer, both of Newport News, all of Va.

[73] Assignee: Vigyan, Inc., Hampton, Va.

[21] Appl. No.: 49,126

[22] Filed: Apr. 19, 1993

[51] Int. Cl.$^5$ ...................... G01N 21/71; G01N 25/00
[52] U.S. Cl. .................................. 250/330; 250/340; 374/9
[58] Field of Search .................. 374/9, 124, 137; 250/340, 330

[56] References Cited

U.S. PATENT DOCUMENTS

| | | | |
|---|---|---|---|
| 3,340,722 | 9/1967 | Gabron et al. | 374/9 |
| 4,716,293 | 12/1987 | Harrick | 250/340 |
| 5,098,195 | 3/1992 | Halyo et al. | 374/9 |
| 5,239,488 | 8/1993 | Markham et al. | 364/557 |
| 5,250,809 | 10/1993 | Nakata et al. | 250/330 |

Primary Examiner—Constantine Hannaher
Attorney, Agent, or Firm—Wallace J. Nelson

[57] ABSTRACT

Apparatus and process for measuring the variation of directional emittance of surfaces at various temperatures using a radiometric infrared imaging system. A surface test sample is coated onto a copper target plate provided with selective heating within the desired incremental temperature range to be tested and positioned onto a precision rotator to present selected inclination angles of the sample relative to the fixed positioned and optically aligned infrared imager. A thermal insulator holder maintains the target plate on the precision rotator. A screen display of the temperature obtained by the infrared imager, and inclination readings are provided with computer calculations of directional emittance being performed automatically according to equations provided to convert selected incremental target temperatures and inclination angles to relative target directional emittance values. The directional emittance of flat black lacquer and an epoxy resin measurements obtained are in agreement with the predictions of the electromagnetic theory and with directional emittance data inferred from directional reflectance measurements made on a spectrophotometer.

17 Claims, 4 Drawing Sheets

DIRECTIONAL EMITTANCE SURFACE MEASUREMENT SYSTEM AND PROCESS

ORIGIN OF THE INVENTION

This invention was made with Government support under Contract NAS1-19505 awarded by NASA, and accordingly, the Government has certain rights in this invention.

FIELD OF THE INVENTION

This invention relates to measuring systems in general and relates specifically to emissivity measurements of surface specimens at various temperatures and angles using radiometric infrared imaging.

BACKGROUND OF THE INVENTION

The use of different materials in high temperature environments is required in a variety of aerospace, nuclear reactors, solar energy and other applications. Thermal analysis is an important tool in selecting and testing various materials for this use and radiometric measurements are an essential part of a complete thermal analysis of a material. Commercially available infrared imaging systems are frequently employed for performing radiometric measurements. For absolute radiometric analysis, knowledge of the radiant properties of the surface under investigation is required. For opaque materials, the knowledge of surface emittance is sufficient, because the reflectance can be inferred from the emittance using Kirchhoff's law. In general, the emittance of a surface is a function of wavelength, temperature, direction and surface conditions, such as roughness, oxide layers, physical and chemical contamination and, in the case of dielectric materials, the grain structure.

When specifying emittance, the wavelength and direction at which emittance is obtained needs to be specified. Monochromatic or spectral emittance is used to indicate emittance at a certain wavelength, while total emittance implies emittance integrated over all wavelengths. Directional emittance implies emittance in a specific direction, while hemispherical emittance implies emittance integrated over the entire hemispherical space. The monochromatic hemispherical emittance is the ratio of the hemispherical emittance of the surface to the hemispherical emittance of a black body at the same wavelength and temperature. The monochromatic hemispherical emittance decreases with increasing wavelength for metals, and generally increases with increasing wavelength for electric nonconductors. For metals, the monochromatic hemispherical emittance increases with increasing temperature and is approximately proportional to the square root of the absolute temperature.

For electric nonconductors, the variation of monochromatic hemispherical emittance with temperature is not very clear, but there is evidence that the emittance varies very slowly with temperature. The total hemispherical emittance is obtained by integrating over all wavelengths from zero to infinity. The directional angular emittance is defined as the ratio of emitted intensity in a specific direction to the intensity of black body radiation at the same temperature. The distribution of emittance for most surfaces is generally dependent upon the inclination angle and the angle of rotation, while for isotropic surfaces, emittance only varies with inclination angle. A diffuse surface is defined as a surface whose emittance is uniform in all angular directions. A black body is a diffuse emitter of radiant energy. Two additional qualifiers are needed for reflectance. A diffusely reflecting surface reflects a single incident ray over all angles with uniform intensity. A specular reflector reflects a single incident ray as a single ray at a reflection angle equal to the incidence angle. A surface generally behaves specularly when the surface roughness is very small compared to the wavelength of incident radiation.

There are extensive tabulations of total hemispherical and total normal emittance data in the literature but there are some discrepancies between published data mainly due to variations in surface conditions. Also, the majority of published data give total emittance, while for radiometry using bandwidth limited infrared imagers, the emittance needs to be integrated over the bandwidth of the infrared imager. To complicate matters further, most infrared imagers do not have a uniform spectral response throughout their system before being integrated over the desired bandwidth. Therefore, for accurate radiometric work, it is necessary to measure the spectral hemispherical emittance of the surface under investigation in the bandwidth of the infrared imager, then weigh the data with respect to the relative spectral response of the imager. The data is then integrated over the bandwidth of the imager. The relative spectral response of the imager may be measured with a spectroradiometer/monochromater system or may be supplied by the Infrared Imager manufacturer.

Some applications require infrared imaging of targets with surface curvature. If the purpose of the measurements is to obtain an average surface temperature, then the hemispherical emittance will be sufficient. But if detailed surface temperature variations on curved surfaces are required, then the directional variation of emittance for the surface material is needed. Experimental data for variation of directional radiation properties are limited but the electromagnetic theory provides the approximate variation of the directional emittance of metals and electric nonconductors under special conditions. Since most applications of radiometric infrared imaging in aerospace research involves targets with surface curvature, a simple measurement technique for accurately measuring the variation of directional emittance of surfaces using infrared imaging systems would prove a valuable research tool.

It is therefore an object of the present invention to provide an apparatus for measuring the variation of directional emittance of a surface using infrared imaging system.

Another object of the present invention is a process for measuring the variation of directional emittance of a surface at various temperatures with an infrared imaging system.

A further object of the present invention is a process of measuring the directional emittance of flat surfaces at various angles to simulate curvatured target surfaces.

SUMMARY OF THE INVENTION

According to the present invention the foregoing and additional objects are attained in the preferred embodiment of the invention by employing an infrared imager to obtain specific measurements of directional emittance for specific test specimens and comparing the results obtained with the electromagnetic theory predicted directional emittance values for these same specimens.

For the electromagnetic theory predicted directional emittance values it is assumed that (1) the theory is restricted to wavelengths larger than the visible; (2) the surface is clean and optically smooth; (3) the surface is isotropic; (4) magnetic permeability of the surface is equal to that of vacuum; (5) there is no accumulation of static charge; and (6) no externally produced electrical conduction currents are present. These are theoretical factors. References as to the effects of static charge or currents on apparent emittances are discussed in the inventors' technical paper entitled "Directional Emittance Corrections for Thermal Infrared Imaging". This paper was presented at the SPIE Thermosense Symposium Proceedings held at Orlando, Fla. Apr. 20–24, 1992 and is incorporated herein by reference.

The apparatus of the present invention was used for determining the directional emittance of flat black lacquer and red Stycast (an epoxy resin), two materials used extensively at NASA's Langley Research Center for aero-thermal wind tunnel studies. Other suitable test coatings would include various thermal resistant plastics, paints, ceramics, metal films, oxides, nitrides, sulfides, and others. The coating thickness and composition must be uniform, to the determined tolerance, over the wind area.

The apparatus of the present invention utilized a commercially available radiometric infrared imager, a heated target plate and a precision rotator. In the specific examples disclosed herein, an Agema 880 infrared imager with the twelve degree lens and the long pass filter limiting its spectral response to the 7.5 to 14 micrometer bandwidth, was employed.

Any metallic thermal conductor formed of high thermal conducting material to assure uniform temperature, may be employed for the target plates. Copper target plates, 15×15×0.3 cm, were used in the specific examples herein, and heated by self-adhesive heating pads attached to the back face thereof. In the specific examples herein, one copper target plate was provided with a front face coating of flat black lacquer and one copper target plate provided with a thin layer of red Stycast on the front face thereof. A suitable thermal insulator, such as for example, Bakelite served as the holder to secure the target plates on the precision rotator. The target plate holder served as a thermal insulator preventing significant heat loss from the heated target plate to the rotator. The heated target plate was set along the optical axis of the infrared imager, with the imager focus set such that the depth of field was optimized to the rotation of the plate. The distance between the imager and the target plate was maintained constant for all tests. The entire experimental apparatus was surrounded with white cardboard on all sides to insure that all the surroundings were isothermal and insure that incident radiation on the heated target plate from the surroundings was uniform in all directions and free of drafts.

The experimental procedure involved heating the target plate and allowing it to reach equilibrium at a temperature controlled at the desired level, and then rotating the target plate along its central axis, thus varying the viewing angle with respect to the surface normal, and measuring the apparent surface temperature of the target at each rotation angle. The surface temperature at each target plate orientation were obtained using the accompanying image processing hardware and software for the infrared imager. The value of the emittance used in the software for converting raw data into absolute temperatures was the normal emittance value over the 8 to 12 micrometer bandwidth, weighed with respect to the relative spectral response of the imager. The measured temperatures at various inclination angles were used to calculate the directional emittance.

BRIEF DESCRIPTION OF THE DRAWINGS

A more complete appreciation of the invention and many of the attendant advantages thereof will be readily apparent as the same becomes better understood by reference to the following detailed description when considered in connection with the accompanying drawings wherein.

DETAILED DESCRIPTION

Figure 1:
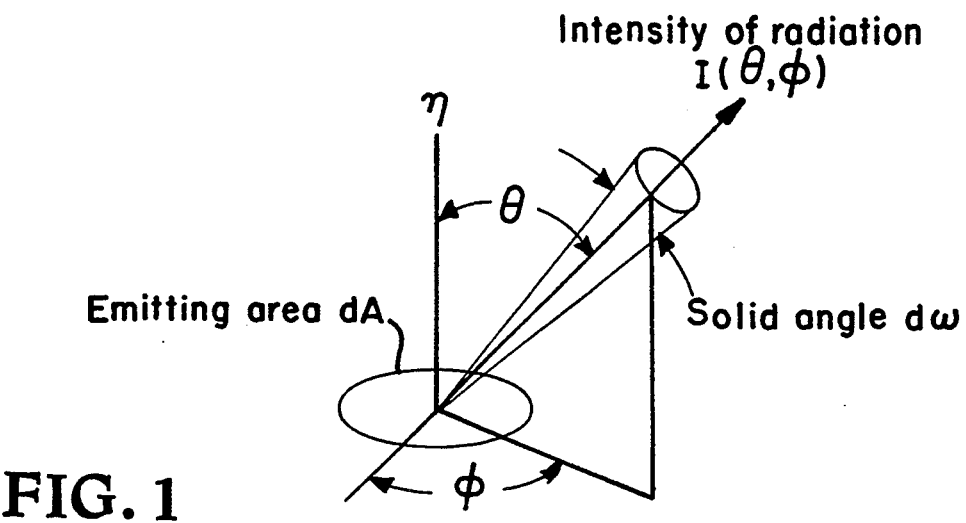
FIG. 1 is a schematic representation of the distribution of emittance dependency on the inclination angle and the rotational angle.

Referring now to the drawings, FIG. 1 is a schematic illustration indicating how the distribution of emittance is generally dependent upon the inclination angle $\theta$, and rotational angle $\phi$. For isotropic surfaces, emittance only varies with inclination angle.

Figure 2:
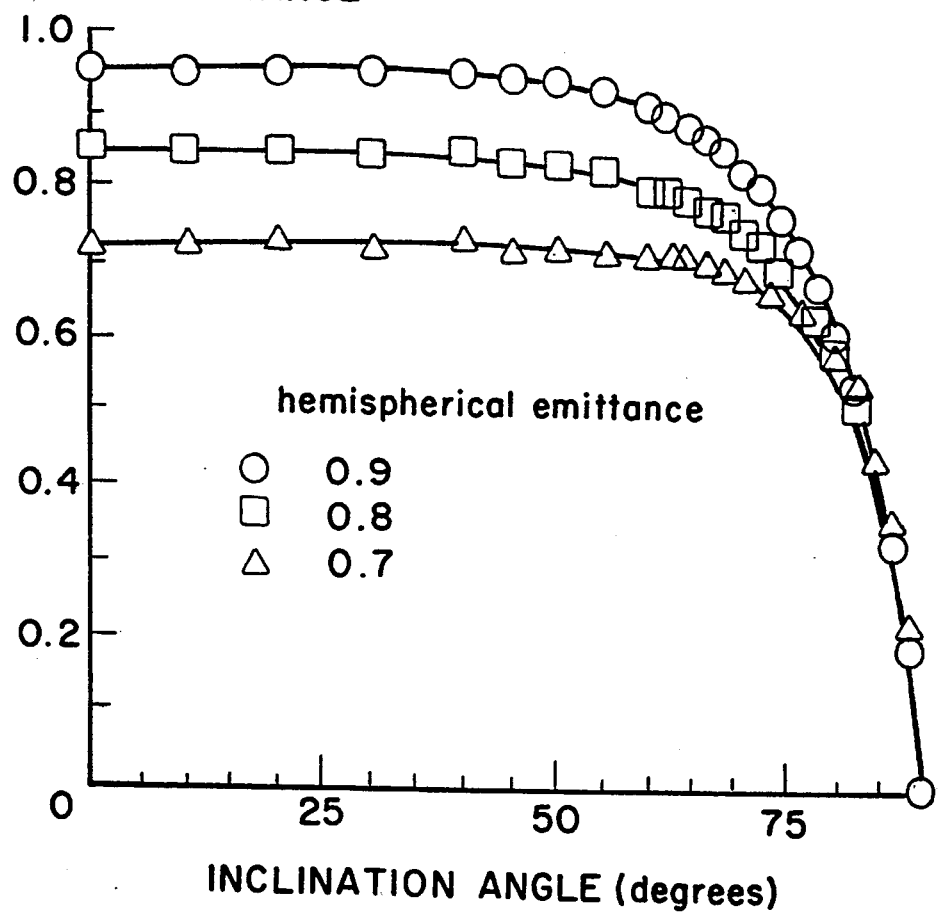
FIG. 2 is a graphical illustration of the variation of directional emittance values obtained from the electromagnetic theory for surfaces having specific hemispherical emittance values.

FIG. 2 graphically indicates the variation of directional emittance values obtained from the electromagnetic theory for surfaces having hemispherical emittances of 0.9, 0.8 and 0.7. As shown therein, the emittance is essentially constant for inclination angles less than 60°, then it drops sharply to zero.

Figure 3:
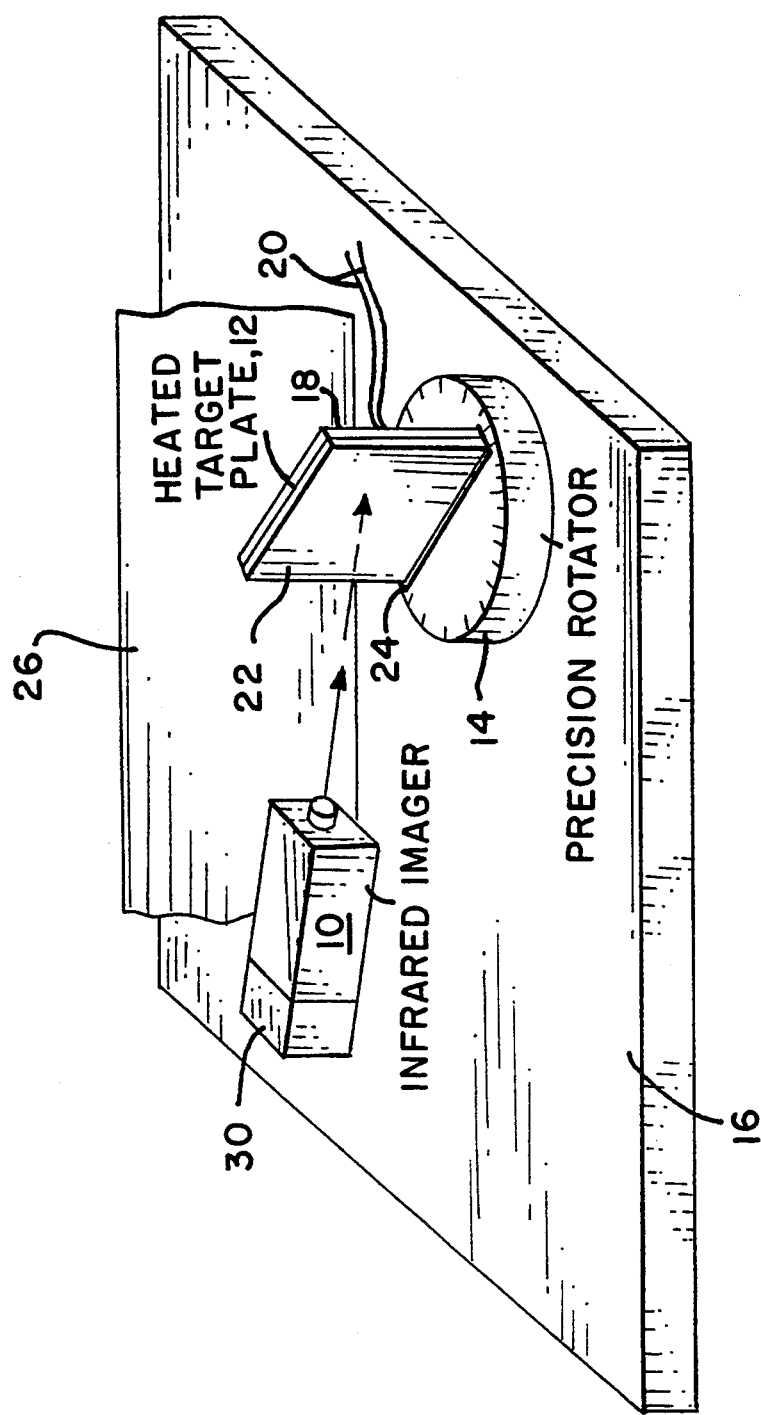
FIG. 3 is a schematic illustration of the test apparatus of the present invention.

Referring now to FIG. 3, the apparatus of the present invention consists essentially of a radiometric infrared imager 10, a heated target plate, generally designated by reference numeral 12, and a precision rotator 14, all mounted on an optical table 16. Two commercially available radiometric infrared imaging systems were utilized, but all the data presented herein were generated with the Agema 880 Infrared Imager with a twelve degree lens and a long pass filter limiting its spectral response to the 7.5 to 14 micrometer bandwidth. Two heated target plates used in the specific examples herein were 15×15×0.3 cm copper plates. A self-adhesive heating pad, 15×15 cm, and designated by reference numeral 18, was employed to heat each target plate 12. Heating pad 18 in this specific example has a power rating of 100 Watts at 115 VAC and is attached to the back face of each copper target plate. Heating pad 18 is powered through wires 20 by a variable voltage output AC power transformer, or Variac, and provided with a temperature sensor (not shown) to provide control or monitoring of the target plate average temperature.

The front face coating 22 on each copper target plate 12 is selected from the group of coatings consisting of black lacquer and red Stycast. Stycast is a tradename for a free flowing, low cost, low viscosity, casting resin of filled epoxy type, and available from Emerson and Cumming Corporation of Canton, Mass. The black lacquer coating is provided by spray painting three layers of flat black lacquer thereon. Sufficient time is provided between each consecutive spray coating to ensure that the lacquer has dried. No polishing or sanding was carried out on the lacquer surface. A thin layer of red Stycast was set and cured on the front face of the other copper target plate. The final thickness of the Stycast was 0.16 cm.

A suitable thermal insulating support, such as for example, Bakelite holder 24, was utilized to set the target plates 12 on the precision rotator 14 and served as a thermal insulator preventing significant heat loss from the heated target plate 12 to the rotator. The heater target plate 12 was set along the optical axis of the infrared imager 10, with the imager and the center of the target plate maintained at 63.5 cm for all the tests in the specific embodiments described herein.

The entire apparatus was surrounded on all sides with white cardboard, a portion of which is schematically shown, and designated by reference numeral 26. Cardboard 26 insures that all the surroundings are isothermal so that incident radiation on the heated target plate 12 from the surroundings is uniform in all directions. In addition, cardboard 26 serves to eliminate specular illumination of the target from adjacent hot sources, such as people, and also serves to reduce drafts on the test assembly.

The test procedure consists of heating target plate 12 and allowing it to reach equilibrium at a set temperature, and then rotating the target plate along its vertical axis, thus varying the viewing angle of infrared imager 10 with respect to the surface normal, and measuring the apparent surface temperature of target 12 at each rotation angle. The imager gain and offset are set such that imager 10 can handle the temperatures at all angles. The surface temperature at each target plate orientation is calculated by averaging temperatures over an area three pixel wide (0.25 cm) centered around the vertical centerline of plate 12, and 20 pixels high. From slit response measurements on this imager, it has been determined that a width of three pixels is needed to capture approximately 95% of a step change in target temperature. The temperatures are obtained using the accompanying image processing hardware and software for the infrared imager, as represented by block 30.

The value of the emittance used in the software for converting raw data into absolute temperatures was the normal emittance value over the 8 to 12 micrometer bandwidth, weighed with respect to the relative spectral response of the imager. The hemispherical emittances were measured using a Perkin-Elmer model 283-B infrared spectrophotometer and were found to be 0.93 and 0.90, respectively, for flat black lacquer and red Stycast. The normal emittance and the refractive index of flat black lacquer was found to be 0.989 and 1.35 while the same measurements for red Stycast were found to be 0.95 and 1.55. The precision rotator had an accuracy of approximately 0°, 6'. The rotator 14 was rotated from 0 to 30 degrees in 10 degree intervals, from 35 to 60 degrees in five degree increments, from 62 to 86 degrees in two degree increments, with a final measurement taken at 87 degrees. Measurement at inclination angles larger that 87 degrees was impossible due to low signal to noise ratio. Tests on each of the black lacquer and red Stycast materials were repeated three to five times at each set temperature.

Figure 4:
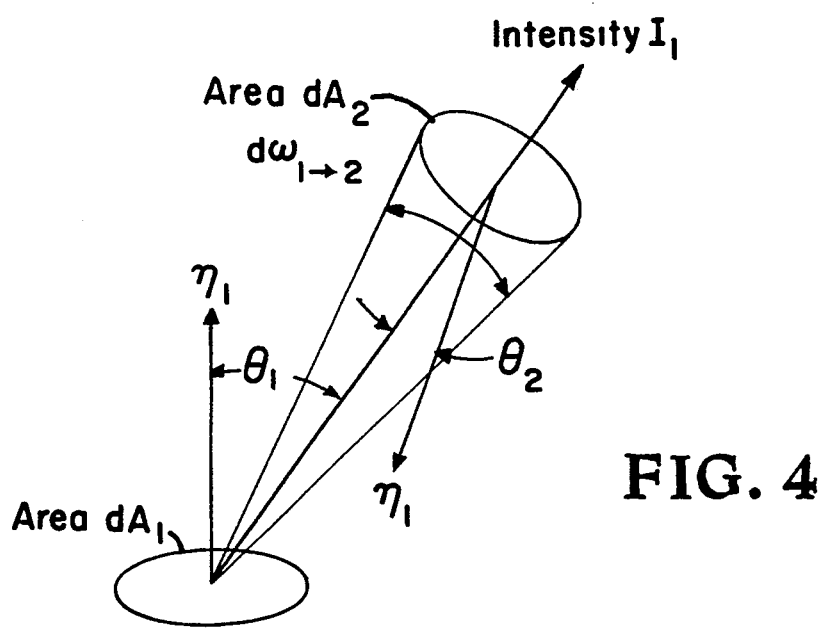
FIG. 4 is a schematic representation of the radiation interchange for the apparatus shown in FIG. 3.

FIG. 4 illustrates a schematic representation of the radiation interchange for the apparatus shown in FIG. 3.

Figure 5:
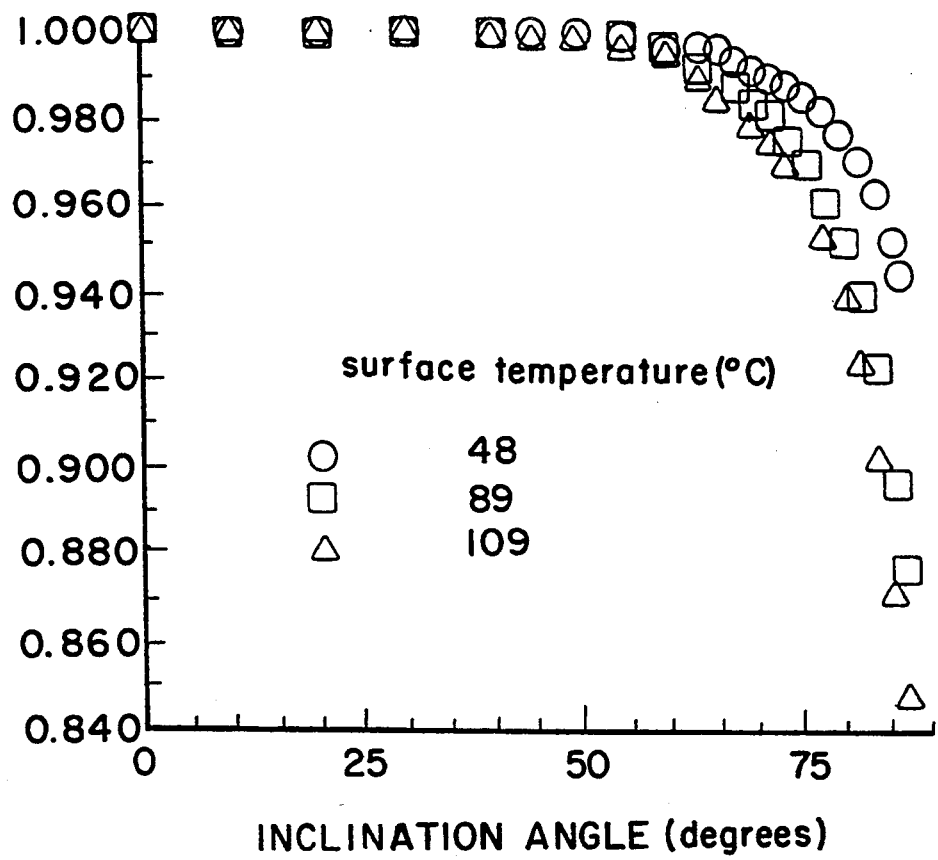
FIG. 5 is a graphical illustration of the variation of the ratio of apparent to actual temperature with inclination angle for flat black lacquer at various temperatures.

FIG. 5 shows the variation of the ratio of apparent to actual temperature with inclination angle for flat black lacquer at temperatures of 48, 89 and 109 degrees Centigrade.

Figure 6:
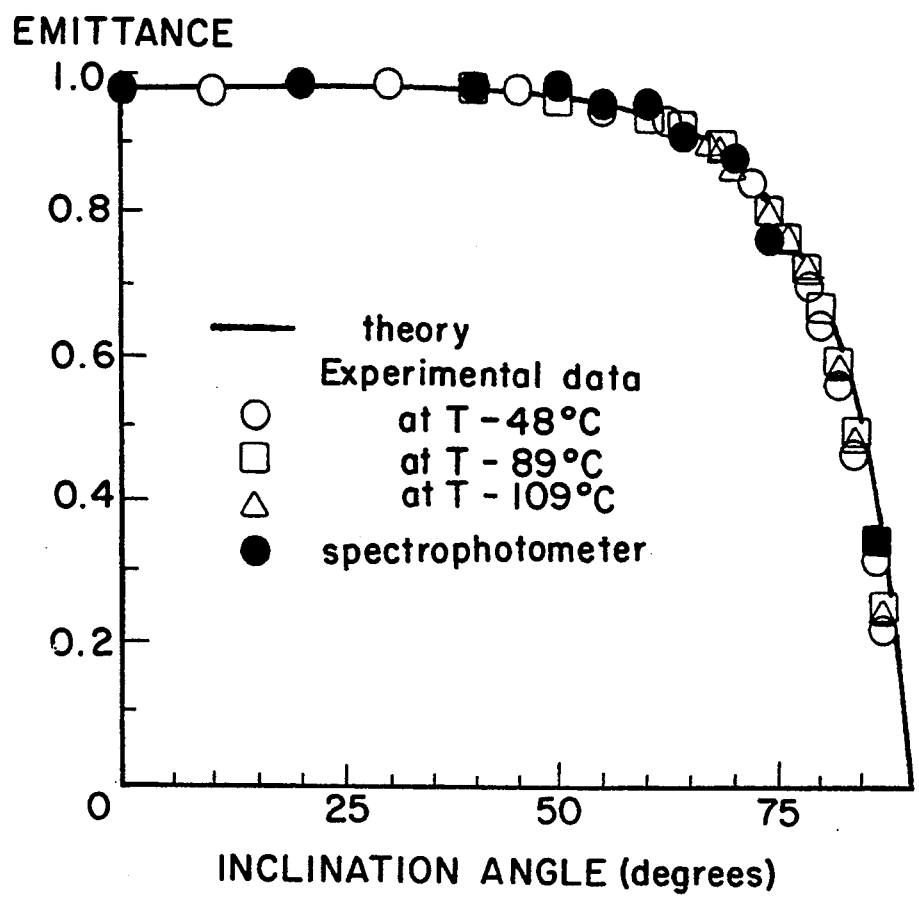
FIG. 6 is a plot of the measured and theoretical directional emittance of flat black lacquer according to the present invention.
Figure 7:
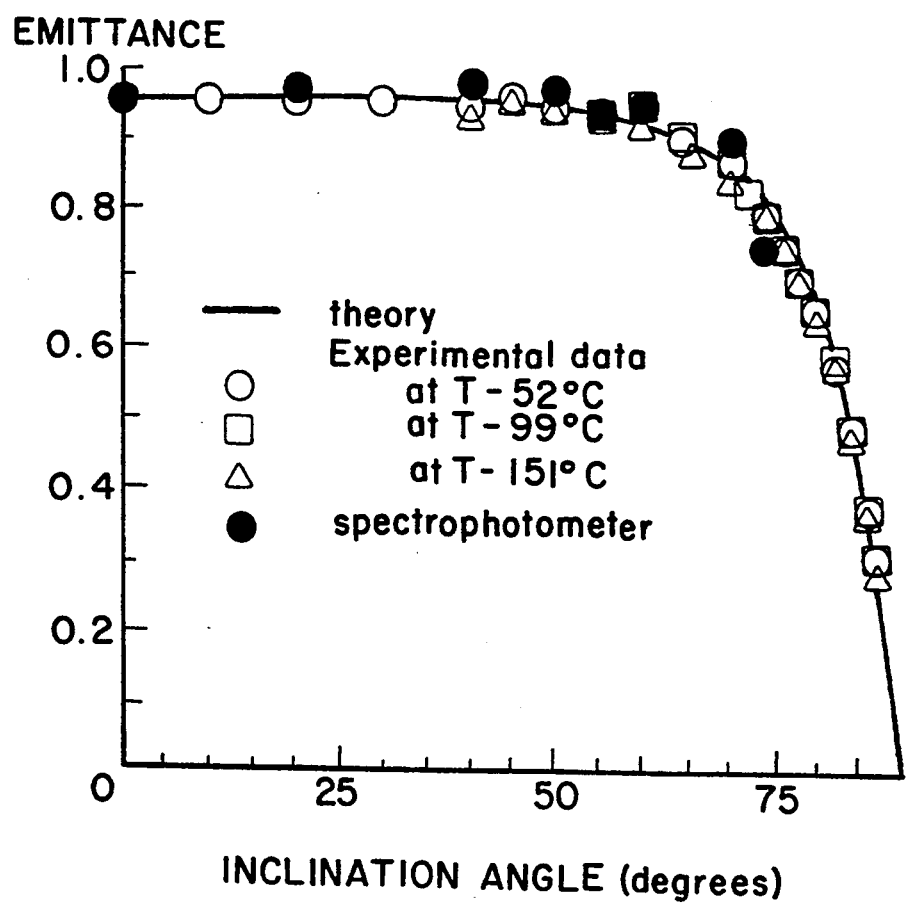
FIG. 7 is a plot of the measured and theoretical directional emittance of red Stycast according to the present invention.

FIG. 6 compares the measurements of direction emittance of flat black lacquer as obtained by the present invention with those obtained by the electromagnetic theory predictions and by spectrophotometer analysis;

FIG. 7 compares the measurements of direction emittance of red Stycast obtained by the present invention with those obtained by the electromagnetic theory predictions and by spectrophotometer analysis.

The electromagnetic theory predictions in the variation of directional emittance as plotted in the drawing FIGS herein neglects the effects of surface conditions on radiative properties by assuming clean, optically smooth surfaces. The expression for monochromatic directional emittance is therefor:

$$\epsilon(\lambda, \theta) = 0.5A \left[ 1 + \frac{(a^2 + b^2 + \sin^2\theta)}{(\cos^2\theta(a^2 + b^2 + 2a\sin\theta\tan\theta + \sin^2\theta\tan^2\theta))} \right] \quad (1)$$

where $$A = \frac{4\cos\theta}{(a^2 + b^2 + 2\cos\theta + \cos^2\theta)} \quad (2)$$

$$2a^2 = [(n^2 - k^2 - \sin^2\theta)^2 + 4n^2k^2]^{0.5} + (n^2 - k^2 - \sin^2\theta) \quad (3)$$

$$2b^3 = [(n^2 - k^2 - \sin^2\theta)^2 + 4n^2k^2]^{0.5} - (n^2 - k^2 - \sin^2\theta) \quad (4)$$

where $\lambda$ is the wavelength, $\theta$ is the angle of emission with respect to the surface normal, n is the refractive index, and k is the extinction coefficient for the surface material. For an electric nonconductor the extinction coefficient is zero, therefore equations 3 and 4 reduce to:

$$a^2 = n^2 - \sin^2\theta \quad (5)$$

$$b^2 = 0. \quad (6)$$

Substituting equations 5 and 6 in equations 1 and 2, and assuming that the quantity "a" is always positive, one can obtain:

$$\epsilon(\lambda, \theta) = 0.5A \left[ 1 + \frac{n^2}{(\cos^2\theta(n^2 - \sin^2\theta + 2(n^2 - \sin^2\theta)^{0.5}\sin\theta\tan\theta + \sin^2\theta\tan^2\theta))} \right] \quad (7)$$

where $$A = \frac{4\cos\theta(n^2 - \sin^2\theta)^{0.5}}{(n^2 - \sin^2\theta + 2\cos\theta(n^2 - \sin^2\theta)^{0.5} + \cos^2\theta)} \quad (8)$$

Hence, by knowing the refractive index of the material, its directional emittance can be found from equations 7 and 8. But usually the refractive index is not known. Integrating equation 7 over the hemisphere results in the monochromatic hemispherical emittance, $\epsilon(\lambda)$:

$$\epsilon(\lambda) = 0.5\epsilon_n(\lambda) \left[ \begin{array}{c} \frac{2}{3} + \frac{1}{3n} + \\ \frac{n(n+1)^2(n^2-1)^2}{2(n^2+1)^3} \ln\frac{n+1}{n-1} + \\ \frac{n^2(n+1)(n^2+2n+1)}{(n^2+1)^2(n-1)} - \\ \frac{4n^3(n^4+1)}{(n^2+1)^3(n-1)^2} \ln n \end{array} \right] \quad (9)$$

where $\epsilon_n(\lambda)$ is the emittance in the direction normal to the surface, $\theta = 0°$, obtained from equation 8:

$$\epsilon_n(\lambda) = \frac{4n}{(n+1)^2}. \quad (10)$$

Even though the above derivations are on monochromatic basis, it is assumed that the emittance of the surface is uniform throughout the bandwidth of the infrared imager, so that the above derivations would hold for integrated values of emittance over the desired bandwidth. If the hemispherical emittance of the surface is known, equations 9 and 10 can be solved simultaneously to yield the normal emittance and the refractive index. Then the refractive index can be used in equation 7 to provide the variation of directional emittance. As discussed hereinbefore, the variation of directional emittance of electric nonconductors having hemispherical emittances of 0.9, 0.8, and 0.7 are plotted in FIG. 2.

The measured temperatures at various inclination angles were used to calculate the directional emittance. For this analysis, the following assumptions were made: the target plate was isothermal, isotropic and opaque, with the background irradiation on the surface distributed uniformly. The amount of radiant energy leaving the infinitesimal area under investigation, $dA_2$, and arriving on the infinitesimal area of the detector of the imager, $dA_1$, as shown in FIG. 4 is given by:

$$dq_{2\to 1} = R(\lambda) F[\epsilon(\theta) E_b + \{1 - \epsilon(\theta)\} G] \quad (11)$$

where $$F = \frac{\cos\theta_1 \cos\theta_2}{r^2} dA_1 dA_2 \quad (12)$$

$R(\lambda)$ is the relative spectral response of imager 10 and r is the distance between imager 10 and target plate 12. The parameter F is analogous to shape factor. For the apparatus shown in FIG. 4, the angles and areas varied as target plate 12 was rotated, but such that the parameter F remained constant. G is the background irradiation on the surface and E is the blackbody emissive power. Therefore, the energy impinging on imager 10 from the infinitesimal area under investigation, when plate 12 has an inclination angle of $\theta$ with respect to the imager can be written as:

$$dq_{2\to 1} = F\left[ \epsilon(\theta) \int_{\lambda_1}^{\lambda_2} \frac{C_1 \lambda^{-5} R(\lambda)}{\exp\left(\frac{C_2}{\lambda T}\right) - 1} d\lambda + \{1 - \epsilon(\theta)\} \int_{\lambda_1}^{\lambda_2} \frac{C_1 \lambda^{-5} R(\lambda)}{\exp\left(\frac{C_2}{\lambda T_\infty}\right) - 1} d\lambda \right] \quad (13)$$

where $\lambda_1$ and $\lambda_2$ are the lower and upper limits of the spectral bandwidth of the imager 10, $C_1$ and $C_2$ are radiation constants, $T_\infty$ is the ambient surroundings temperature, and T is the actual plate temperature. This impinging radiant energy is converted to an apparent temperature $T_a$, in the imaging system assuming diffuse radiative exchange and using the normal surface emittance, $\epsilon_n$:

$$dq_{2\to 1} = F\left[ \epsilon_n \int_{\lambda_1}^{\lambda_2} \frac{C_1 \lambda^{-5} R(\lambda)}{\exp\left(\frac{C_2}{\lambda T_a}\right) - 1} d\lambda + \{1 - \epsilon_n\} \int_{\lambda_1}^{\lambda_2} \frac{C_1 \lambda^{-5} R(\lambda)}{\exp\left(\frac{C_2}{\lambda T_\infty}\right) - 1} d\lambda \right]. \quad (14)$$

Equations 13 and 14 can be combined to give:

$$\frac{\epsilon(\theta)}{\epsilon_n} = \frac{\int_{\lambda_1}^{\lambda_2} \lambda^{-5} R(\lambda) \left[ \frac{1}{\exp\left(\frac{C_2}{\lambda T_a}\right) - 1} - \frac{1}{\exp\left(\frac{C_2}{\lambda T_\infty}\right) - 1} \right] d\lambda}{\int_{\lambda_1}^{\lambda_2} \lambda^{-5} R(\lambda) \left[ \frac{1}{\exp\left(\frac{C_2}{\lambda T}\right) - 1} - \frac{1}{\exp\left(\frac{C_2}{\lambda T_\infty}\right) - 1} \right] d\lambda} \quad (15)$$

Therefore, by knowing the relative spectral response of imager 10, the ambient temperature, the actual target plate temperature, and by measuring the apparent temperature at each inclination angle using infrared imager 10, the relative directional emittance can be estimated using equation 15. Finally, the absolute directional emittance $\epsilon(\theta)$ can be calculated from the relative directional emittance using the normal emittance $\epsilon_n$.

To verify the accuracy of the present invention, the directional emittance of flat black lacquer and red Stycast samples were estimated from reflectance measurements made on a Perkin Elmer model 283B double beam grating spectrophotometer with a Perkin Elmer model 3600 data acquisition system. This equipment provided measurements up to 75 degree inclination angles and was used because of lack of operational goniometric or integrating sphere based reflectance or emittance measurement apparatus for the spectral range of 2.5 to 16 micrometers.

The reflectance measurements on the Perkin Elmer 283B were made with a variable angle reflectance accessory, using an aluminum mirror as a reference. This accessory measures specular reflectance in the plane of radiation incidence at equal angles of incidence and reflection from the target surface. In these measurements, a sample space silver bromide wire grid polarizer set to 45 degree polarization axis, was installed in the sample port ahead of the reflectance accessory to eliminate sample dependent polarization offsets. The target samples and the aluminum mirror were each scanned at the same incidence angles between 20 and 75 degrees under a slit setting which yielded spectral slit widths between 3 and 12 wave-numbers. Data were sampled at one wave-number intervals.

In the absence of additional reflectance measurement attachments and polarizers to equalize the sample and reference beam path lengths, the reference beam was run at the standard length, including a reference beam attenuator to increase the signal dynamic range resulting from the polarizer-caused sample beam attenuation. The spectrophotometer and the sample compartment were purged with dry air with dew-point temperature of $-73°$ C. (200 kelvin).

The sample reflectances were measured over a range slightly larger than the spectral bandpass of the infrared imager. The angular monochromatic specular reflectance of the samples was obtained as follows. Raw reflectance data from the Stycast epoxy and the flat black lacquer sample runs were ratioed to the same wave-number raw data from the aluminum mirror at the same incidence angle, and these ratios were multiplied by the nominal, near normal absolute reflectance of the aluminum mirror. The absolute reflectance of aluminum was obtained from published data for fresh aluminum films.

The diffuse reflectance of the samples were made on a Harrick Praying Mantis diffuse reflectance apparatus of the inverted solid sample type. This was a partial spherical incidence-partial spherical collection device, which partially removed specular reflectance components by means of its alignment. A pressed sulfur disc was used as the working diffuse reflectance. The measurement procedure required the following measurements: the near normal (7 degree nominal) specular reflectances of the samples under test and the references over the same spectral range and with the same sampling interval, the spectral leakage of the diffuse apparatus, scanning of the samples, the sulfur reference, and the no-sample zero over the wavelength range. The data were calculated at each point from:

$$HRx(i) = \frac{\left[\{DRx(i) - Z(i)\} - \{DR1(i) - Z(i)\}\left(\frac{SRx(i)}{Sr1(i)}\right)\right]}{\left[\{DRsu(i) - Z(i)\} - \{DR1(i) - Z(i)\}\left(\frac{SRsu(i)}{Sr1(i)}\right)\right]} Refsu(i) \quad (6)$$

where:
HRx=Hemispherical diffuse reflectance
i=wave-number
DRx=raw sample deflection
Drsu=raw sulfur reference deflection
DR1=raw specular leak deflection
Z=zero deflection
SRx=sample specular reflectance at 7° incidence
SRsu=sulfur specular reflectance at 7° incidence
SR1=specular leak reflectance at 7° incidence
Refsu=sulfur diffuse reflectance The diffuse reflectance data for the sulfur sample closely approximated published data. Unpublished studies at the Langley Research Center have indicated that the total reflectance of samples having relatively smooth surfaces compared with the wavelength can be determined by adding the specular and diffuse reflectances. Therefore, for opaque materials, the monochromatic directional emittance is obtained from the total reflectance using Kirchhoff's law. This procedure is similar to that used in the Hohlraum emittance apparatus, where emittance is determined by measuring the reflectance of a cooled sample as a function of incidence angle and then integrated with respect to the Planck equation. While this is a gross approximation, this procedure should yield acceptable results for the case of sample temperatures being near the temperature of 46° C. at which the reflectance of these samples were measured.

Data were obtained on the flat black lacquer sample at nominal surface temperatures of 48°, 89° and 109° C. The variation of the ratio of the measured apparent temperatures to the actual temperature in kelvin with inclination angle for tile three nominal surface temperatures is shown in FIG. 5. As shown therein, the apparent surface temperatures were equal to the actual surface temperatures for inclination angles up to 55°-60°. The drop in apparent temperature with increasing inclination angles was not significant at lower surface temperatures. This was due to the fact that the contribution of the reflected surroundings radiation in comparison to the emitted energy increased with decreasing surface temperatures. The variation of directional emittance of flat black lacquer measured using the present invention and calculated from equation 15 is presented in FIG. 6. The predictions of the electromagnetic theory and the directional measurements made using the spectrophotometer are also illustrated. The spectrophotometric measurements were in good agreement with the predictions of the electromagnetic theory. The deviation of the spectrophotometric measurements from the theoretical predictions had a mean of 0.004 with a standard deviation of ±0.012. The data measured using the present technique were also in good agreement with predictions of the electromagnetic theory. The three sets of emittance measurements at each inclination angle were averaged, and the deviation of these average values with respect to the theoretical predictions was found to have a mean of 0.001 with a standard deviation of ±0.008.

Data were obtained on the red Stycast sample at nominal surface temperatures of 52°, 99° and 151° C. The variation of directional emittance of red Stycast measured using the apparatus of the present invention and calculated from equation 15 is graphically shown in FIG. 7. The predictions of the electromagnetic theory and the directional measurements made using the spectrophotometer are also included. The spectrophotometric measurements deviated from the theoretical data with a mean of 0.017 and a standard deviation of ±0.012. The three sets of emittance measurements at each inclination angle were averaged, and the deviation of these average values with respect to the theoretical predictions was found to have a mean of 0.017 with a standard deviation of ±0.016.

It is thus seen that the present invention provides a simple measurement process that could provide accurate variation of directional emittance of electric nonconductors over the wavelength range of 7.5 to 14 micrometers and other wavelength ranges depending upon the lens employed. The present invention is considered operable with any infrared bandpass 1.5 to 30 micrometers and with any lens of suitable size to cover the target at normal incidence, as specified with adequate depth of field. It is expected that this technique is equally valid over different bandwidths, and therefore could be applied to the short-wave imagers, operating in the 3 to 5.5 micrometer bandwidth. It is emphasized that these measurements were conducted on electric nonconductor samples having hemispherical emittance of 0.9 or larger in the 7.5 to 14 micrometer bandwidth, and therefore, measurements on samples having hemispherical emittances between 0.7 and 0.9 would further validate this process.

Although the invention has been described relative to a specific apparatus and process, it is not so limited and, there are many variations and modifications of the disclosed apparatus and process that will be readily apparent to those skilled in the art in the light of the above teachings. For example, the distance infrared imager 10 is disposed from the target plate test specimen will vary with the lens employed. Also, other wavelength ranges would be dependent upon the lens employed.

It is therefore to be understood that in the light of the above teachings, the invention may be practiced other than as specifically described herein.

We claim:

1. Apparatus for measuring variations of directional emittance of surfaces at different temperatures comprising:
   a flat surface target plate test specimen;
   means for heating said target plate test specimen over a selected and controlled incremental temperature range;
   an infrared imager disposed at a fixed distance from and in optical alignment with said target plate test specimen;
   means for selectively rotating said target plate test specimen to vary the inclination angle thereof relative to said infrared imager;
   means for measuring target plate temperature data from said infrared imager;
   means for measuring the inclination angle; and
   means for calculating directional emittance values from the measured temperatures from said infrared imager and measured inclination angles.

2. The apparatus of claim 1 wherein said infrared imager is provided with a 12 degree lens and a long pass filter limiting the spectral response thereof to the 7.5 to 14 micrometer bandwidth.

3. The apparatus of claim 1 wherein the fixed distance said infrared imager is disposed from said target plate test specimen is dependent upon the lens employed on the infrared imager and with a 12 degree lens this fixed distance is 63.5 cm.

4. The apparatus of claim 1 wherein said flat surface target plate is a copper plate having a front and a rear face surface area; a test surface coating disposed on said front face surface area of said target plate; said test surface coating being selected from the group of test surfaces consisting of flat black lacquer and an epoxy resin coating.

5. The apparatus of claim 4 wherein the means for selectively rotating said target plate test specimen is a precision rotator providing controlled target rotation in incremental degrees in the minimum range of 0 to 87 degrees.

6. The apparatus of claim 4 wherein the means for heating said target plate is an electric heating pad secured to said rear face surface area of said target plate.

7. The apparatus of claim 6 including a thermal insulating holder retaining said target plate fixed on said precision rotator.

8. The apparatus of claim 6 wherein the target plate is incrementally heated by said electric heating pad for test measurement in the temperature range of 48° to 109° C.

9. A process for determining variations of directional emittance of test surfaces at various temperatures and at various inclination angles, comprising:
   providing a target plate having a flat surface test coating on a front face thereof;
   heating the target plate incrementally in the temperature range of 48° to 109° C.;
   providing an infrared imager in optical alignment with the test surface coated target plate;
   rotating the test surface coated target plate relative to the infrared imager at controlled increments from 0 to 87 degrees;
   employing the infrared imager to measure target plate temperature;
   measuring the target inclination angle; and
   converting the temperature and target inclination angle data into target directional emittance values.

10. The process of claim 9 wherein the flat surface test coating on the target plate is selected from the group of coatings consisting of flat black lacquer and an epoxy resin.

11. The process of claim 10 wherein the target plate is a copper plate and the flat surface test coating is flat black lacquer, and including the steps of:
   spray coating a first layer of flat black lacquer on the front face of the copper plate;
   air drying the first layer of flat black lacquer at room temperature;
   spray coating a second layer of flat black lacquer over the first layer and permitting it to air dry at room temperature; and
   spray coating a third layer of flat black lacquer over the second layer and permitting it to air dry at room temperature.

12. The process of claim 10 wherein the target plate is a copper plate and the flat surface test coating is an epoxy resin coating cast at a thickness of approximately 0.16 cm on the front face of the copper plate.

13. The process of claim 9 wherein the target plate is a metallic thermal conductor formed of a high thermal conducting material to assure uniform temperature when treated.

14. The process of claim 13 wherein the target plate is a copper plate 15×15 by 0.3 cm.

15. The process of claim 13 wherein the step of heating the target plate is accomplished by adhesively securing an electric heating pad to the rear face of the target plate and opposite to the front face having the test coating thereon.

16. The process of claim 15 wherein the electric heating pad is provided with a self-adhesive surface for being adhesively secured to the rear face of the target plate and wherein the heating pad is 15×15 cm and has a power rating of 100 Watts at 115 VAC.

17. The process of claim 9 wherein the step of converting the temperatures and target inclination data into relative target directional emittance values at selected incremental target temperatures and inclination angles is performed by automated computer analysis of the equation:

$$\frac{\epsilon(\theta)}{\epsilon_n} = \frac{\int_{\lambda_1}^{\lambda_2} \lambda^{-5} R(\lambda) \left[ \dfrac{1}{\exp\left(\dfrac{C_2}{\lambda T_a}\right) - 1} - \dfrac{1}{\exp\left(\dfrac{C_2}{\lambda T_\infty}\right) - 1} \right] d\lambda}{\int_{\lambda_1}^{\lambda_2} \lambda^{-5} R(\lambda) \left[ \dfrac{1}{\exp\left(\dfrac{C_2}{\lambda T}\right) - 1} - \dfrac{1}{\exp\left(\dfrac{C_2}{\lambda T_\infty}\right) - 1} \right] d\lambda}$$

where
$\lambda$ = wavelength
$\lambda_1, \lambda_2$ = lower and upper wavelengths for infrared imager
$C_2$ = radiation constant
$T_a$ = apparent temperature
$T_\infty$ = ambient surrounding temperature
$R(\lambda)$ = relative spectral response of infrared
$T$ = actual temperature
$\epsilon(\theta)$ = directional emittance
$\epsilon_n$ = normal emittance and, where the apparent temperature at each inclination angle is measured using the infrared imager, and the relative spectral response of the imager, the ambient temperature and the actual target plate temperature are known.

* * * * *